United States Patent [19]
Salimbeni et al.

[11] Patent Number: 5,804,583
[45] Date of Patent: Sep. 8, 1998

[54] PYRIMIDINONE DERIVATIVES FUSED TO NITROGEN HETEROCYCLES HAVING A II ANTAGONISTIC ACTIVITY

[75] Inventors: Aldo Salimbeni; Davide Poma; Anna Renzetti; Carlo Scolastico, all of Lomagna, Italy

[73] Assignee: Istituto Luso Farmaco D'Italia, Milan, Italy

[21] Appl. No.: 768,791

[22] Filed: Dec. 18, 1996

Related U.S. Application Data

[63] Continuation of Ser. No. 464,849, filed as PCT/EP94/00139, Jan. 20, 1994, abandoned.

[30] Foreign Application Priority Data

Jan. 22, 1993 [IT] Italy .................. MI93A0100

[51] Int. Cl.$^6$ .................. A61K 31/505; A61K 31/53; C07D 251/00; C07D 487/00
[52] U.S. Cl. .................. 514/258; 514/241; 514/245; 544/180; 544/194; 544/195; 544/208; 544/211; 544/213; 544/214; 544/215; 544/216; 544/220; 544/223; 544/244; 544/279; 544/281
[58] Field of Search ................... 514/241, 245, 514/258; 544/180, 194, 195, 208, 211, 213, 214, 215, 216, 220, 223, 244, 279, 281

[56] References Cited

U.S. PATENT DOCUMENTS

| | | | |
|---|---|---|---|
| 5,231,094 | 7/1993 | Bru-Magniez et al. | 514/233.2 |
| 5,250,521 | 10/1993 | Allen et al. | 514/81 |
| 5,387,747 | 2/1995 | Bru-Magniez et al. | 514/233.2 |

FOREIGN PATENT DOCUMENTS

| | | |
|---|---|---|
| 400 974 | 12/1990 | European Pat. Off. . |
| 411 766 | 2/1991 | European Pat. Off. . |
| 435 827 | 7/1991 | European Pat. Off. . |
| 521 768 | 1/1993 | European Pat. Off. . |
| WO 91/15209 | 10/1991 | WIPO . |
| WO 93/17024 | 9/1993 | WIPO . |

*Primary Examiner*—Mukund J. Shah
*Assistant Examiner*—Brenda Coleman
*Attorney, Agent, or Firm*—Walter H. Schneider

[57] ABSTRACT

Derivatives of bicyclic heterocycles comprising a pyrimidone ring fused to another 5, 6, or 7 membered nitrogen heterocycle which is C-substituted, through a methylene bridge, by a biphenyl group.

4 Claims, No Drawings

PYRIMIDINONE DERIVATIVES FUSED TO NITROGEN HETEROCYCLES HAVING A II ANTAGONISTIC ACTIVITY

This application is a continuation of application Ser. No. 08/464,849 filed Aug. 14, 1995, now abandoned which is a 371 of PCT/EP94/00139, filed Jan. 20, 1994.

The present invention relates to derivatives of bicyclic heterocycles, consisting of a pyrimidinone ring fused to another 5, 6 or 7 membered nitrogen heterocycle, which is C-substituted, through a methylene bridge, by a biphenyl group.

The renin-angiotensin system (RAS) is a proteolytic cascade which plays a paramount role in the control of blood pressure and is apparently involved in the onset and the maintainement of some cardiovascular disorders, such as hypertension and cardiac decompensation.

The octapeptide hormon angiotensin II (A II), the final product of RAS, mainly forms in the blood following to the degradation of angiotensin I, carried out by the ACE enzyme, which is located in endothelium of blood vessels, lungs, kidney and many other organs. Such an hormon exerts a strong vasoconstricting action on arteries, due to its interaction with specific receptors located on the cell membranes.

One of the possible ways to control RAS is the A II antagonism at the receptor level. Some peptide analogues of A II (for example saralasin, sarmesin) are known to competitively block the interactions of said hormon, however the use thereof, both experimentally and clinically, is restricted by a partial agonistic activity and by the lack of activity by the oral route.

Recently, a number of derivatives having a non-peptide structure were described to have II antagonist activity. Examples of these compounds are reported in EP EP028834, EP245637, EP253310, EP291969, EP324377, EP400835, EP400974, EP411766, EP425921 and in the articles of A. T.Chiu et al. Eur.J.Pharm.Exp.Therap., 157, 13–21 (1988), P. C. Wong et al. J.Pharm.Exp.Therap., 247, 1–7 (1988), Hypertension, 13 489–497 (1989).

The novel compounds of the invention have A II antagonistic Properties and therefore they can be used in various cardiovascular disorders, such as hypertension, cardiac decompensation, intraocular hypertension, glaucoma or in the post-treatment of miocardial infarction or also in some renal diseases or in hyperaldosteronism. The compounds claimed in the present invention, including possible tautomers and enantiomers, have the general formulae (I) and (I')

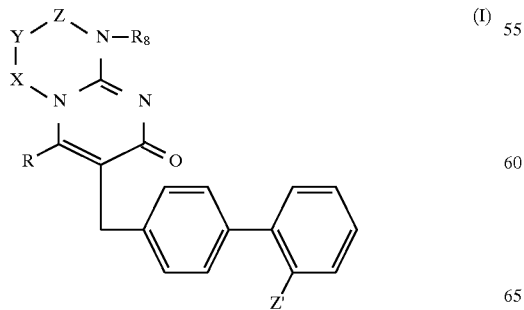

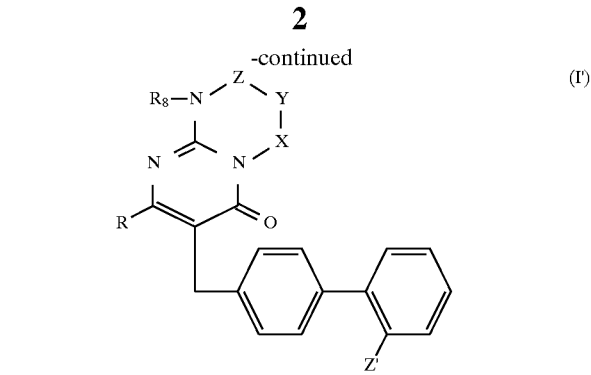

in which:

Z' can be a $COOR_1$ group (wherein $R_1$ can be hydrogen, straight or branched $C_1$–$C_5$ lower alkyl), $SO_3H$, $PO_3H$, $NHSO_2CF_3$ or a tetrazole group of general formula (IIa) or (IIb)

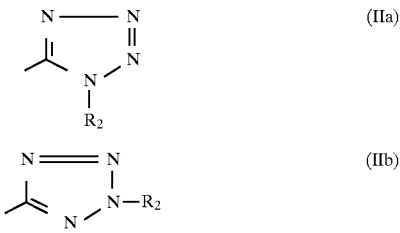

wherein $R_2$ can be hydrogen or lower alkyl,

R can be straight, branched or cyclic $C_1$–$C_6$ lower alkyl, or $C_1$–$C_6$ lower alkenyl;

$R_8$ can be hydrogen, straight, branched or cyclic $C_1$–$C_6$ lower alkyl, a lower alkenyl or alkynyl group or a $COR_{10}$ group, wherein $R_{10}$ can be hydrogen, straight, branched or cyclic $C_1$–$C_6$ lower alkyl, or a $NR_5R_6$ group, wherein R5 and $R_6$ can be independently hydrogen, straight, branched or cyclic $C_1$–$C_6$ lower alkyl, or lower alkenyl or lower alkynyl;

X, Y, Z can be independently $CR_3R_4$, C=O, =C—$R_3$, =N, $(CH_2)_n$, with the provisos that X and Z are always different from =N and that, when X and/or Z are C=O, Y is different from Co, in which n can be 0, 1 or 2, $R_3$ can be hydrogen, straight, branched or cyclic $C_1$–$C_6$ lower alkyl, lower alkenyl or alkynyl or a $NR_5R_6$ group, wherein $R_5$ and $R_6$ have the meanings reported above, $R_3$ can also be a $COR_7$ group, wherein $R_7$ can be hydrogen, straight, branched or cyclic $C_1$–$C_6$ lower alkyl, or a $NR_5R_6$ group with the meanings reported above, finally $R_3$ can be a $NR_9CONR_5R_6$ group, wherein $R_5$ and $R_6$ have the meanings reported above and $R_9$ can be hydrogen or methyl;

$R_4$ can be hydrogen or straight, branched or cyclic $C_1$–$C_6$ lower alkyl.

X—Y—Z form, together with the pyrimidinone ring to which they are linked, a heterocyclic moiety preferably selected from the following ones, in which $R_3$, $R_4$ and $R_8$ are preferably hydrogen or a straight, branched or cyclic $C_1$–$C_4$ lower alkyl.

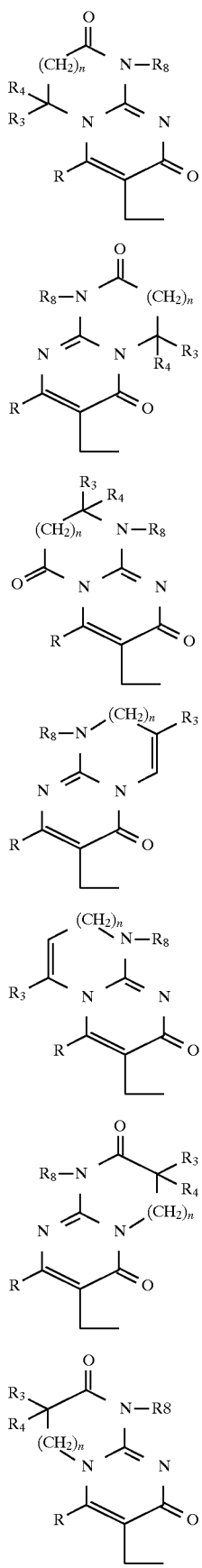

(a)

(b)

(c)

(d)

(e)

(f)

(g)

The compounds of the invention form salts with various organic and inorganic acids and bases, which salts are also part of the invention. Said salts include ammonium salts, salts with alkali metals such as sodium and potassium, salts with alkaline-earth metals such as calcium and magnesium, salts with organic bases such as dicyclohexylamine, N-methyl-D-glucamine, salts with amino acids such as arginine, lysine and the like.

The salts with organic and inorganic acids comprise hydrochloric, hydrobromic, sulfuric, phosphoric, methanesulfonic, toluenesulfonic, maleic, fumaric, camphorsulfonic acids and the like.

Moreover, the invention relates to the processes for the preparation of the compounds of general formulae (I) and (I').

A first method (method A) comprises reacting the compounds of general formula (III)

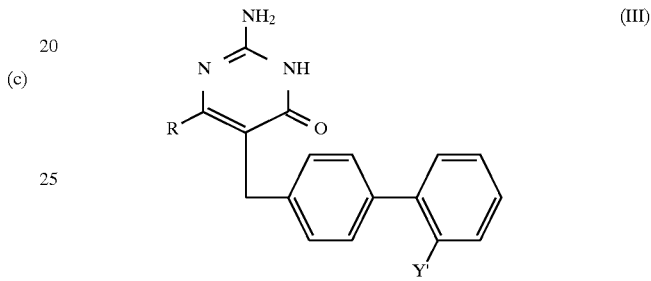

in which:

R has the same meanings as in the formulae (I) and (I'),

Y' can be $NO_2$, CN, $COOR_{11}$ (wherein $R_{11}$ is straight or branched lower alkyl) or a tetrazole group of formula (IIa) or (IIb), in which $R_2$ can be lower alkyl or a protecting group, such as triphenylmethyl, with compounds of general formula (IV)

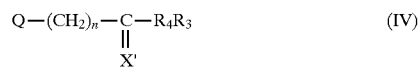

in which:

$R_3$, $R_4$ and n have the same meanings as in formulae (I) and (I'), with the proviso that, when X' is oxygen, $R_4$ is not present, X' is oxygen, halogen, such as bromine, chlorine, iodine or a tosylate or mesylate group or a COOH, COCl, COBr or —NCO group, Q can be halogen, such as bromine, chlorine, iodine, or a —NCO, COBr, COCl, COOH, $COOR_{12}$ group (wherein $R_{12}$ is lower alkyl), to give compounds of formula (I) or (I'), in which Z' is the same as Y' and subsequently, transforming, if necessary, the residue Y' into the residue Z', wherein Z' has the meanings as in formulae (I) and (I').

The compounds of general formula (IV) are preferably haloacids or their derivatives (such as lower alkyl ester or acyl halides) of formula HOOC—$(CH_2)_n$—$CR_3R_4$—Hal or HOOC—$CR_3R_4$—$(CH_2)_n$—Hal, in which $R_3$ and $R_4$ are hydrogen or $C_1$-$C_4$ lower alkyl groups, n is 0, 1, 2, Hal is bromine or chlorine halocarbonyl compounds or their protected forms (such as acyclic or cyclic acetals or ketals) of formula Hal—$(CH_2)_n$—CO—$R_3$ which $R_3$ is hydrogen or $C_1$-$C_4$ lower alkyl, n is , 2, Hal is bromine or chlorine.

The reaction can be carried out, depending on the meanings of X' and Q, in various organic solvents, preferably aprotic polar solvents such as DMF, N-methylpyrrolidin-2-one (NMP), DMSO, pyridine, or apolar solvents, such as benzene, toluene, CHCl$_3$, CH$_2$Cl$_2$, in the absence or in the presence of a base which can be either organic, such as pyridine, diisopropylethylamine, dimethylaminopyridine, triethylamine or inorganic, such as alkali metal hydrides, alkoxides or carbonates.

The reaction can also be carried out in the presence of activating and coupling agents, such as dicyclohexylcarbodiimide (DCC), 1-hydroxybenzotriazole (HOBT), diphenylphosphorylazide (DPPA), carbonyldiimidazole (DCI). The temperature can range from 0° C. to the boiling point of the solvent.

The condensation reaction can yield a single regioisomer or mixtures of regioisomers, which can easily be separated by fractional crystallization or the conventional chromatographic techniques.

In some cases, for example when compounds of formula (IV) in which Q is a carboxyl group and X' is halogen are reacted, the intermediate compounds of formula (V) can be isolated

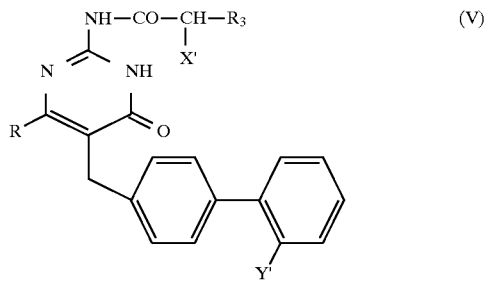

in which:
R, R$_3$ have the same meanings as in formulae (I) and (I'),
X' is chlorine, bromine, iodine, Y' has the same meanings as in formula (III), which intermediates can easily be cyclized to compounds of formula (I) and (I'), in which Z' is the same as Y', by treatment with bases, such as alkali metal hydrides, alkoxides or carbonates, in aprotic solvents such as DMF, DMSO, NMP, THF, DME, ethyl ether.

Thereafter the residue Y' can be transformed, if necessary, into the residue Z', wherein Z' has the same meanings as in formulae (I) and (I').

When Y' is an alkoxycarbonyl group, the compound can be subjected to hydrolysis with either acids (hydrochloric, trifluoroacetic, formic, acetic acids in protic solvents such as water-lower alcohols mixtures, or in aprotic solvents such as CH$_2$Cl$_2$, dioxane) or alkali (alkali hydroxides in water-lower alcohols mixtures) at temperatures from 20° to 80° C.

When Y' is a CN group, it can be subjected to hydrolysis by treatment with strong acids or bases, preferably with aqueous hydrochloric acid/glacial acetic acid 1:1 mixtures under reflux, or with NaOH in ethanol or ethylene glycol at a temperature from 20° C. to the solvent's reflux.

The CN group could also be converted into the corresponding tetrazole derivative by treatment with NaN$_3$ and NH$_4$Cl in DMF at temperatures from 30° to 120° C., or better by 1,3-dipolar addition of trialkyl or triaryl stannyl azides in solvents such as toluene or xylene at temperatures from 110° to 130° C.

When Y' is a tetrazole group protected with a triphenylmethyl group, the latter can be removed by treatment with acetic, trifluoroacetic or hydrochloric acids or by hydrogenolysis.

When Y' is NO$_2$, this can be transformed into the NH$_2$ group by, for example, catalytic hydrogenation in the presence of Ni Raney, in alcohol at atmospheric pressure or under pressure. Said group can subsequently be converted into the —NHSO$_2$CF$_3$ group by treatment with trifluoromethanesulfonic acid chloride or anhydride in CH$_2$Cl$_2$, CHCl$_3$ or in an aromatic solvent, such as benzene, toluene, pyridine in the presence of a base such as triethylamine or pyridine.

The intermediate pyrimidinone derivatives of formula (III) can be prepared with methods known in literature, for example reacting guanidine or the salts thereof with the substituted β-ketoesters of general formula (VI)

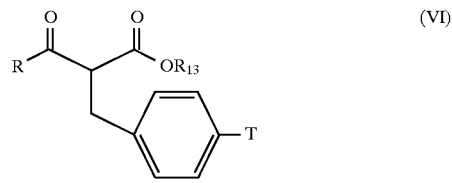

in which:
T is —C$_6$H$_4$—Q—Y' wherein Y' has the same meanings as in formula (III), R has the same meanings as in formulae (I) and (I'), R$_{13}$ is methyl or ethyl, which are in their turn prepared by alkylation of the corresponding, easily accessible non substituted β-ketoesters with per se known bromomethylbiphenyl derivatives, as it will be further explained in the examples.

The reaction can be carried out in protic solvents such as lower alcohols (methanol, ethanol, isopropanol) or in water or in a mixture thereof or in an aprotic solvent, such as benzene or toluene, in the absence or in the presence of bases such as alkali or alkaline-earth metal alcoholates (CH$_3$ONa, C$_2$H$_5$ONa, tert-ButOK), hydroxides or carbonates.

The temperature can vary from the room one to the solvent's boiling temperature. The reaction can also be effected in acid medium with acetic or hydrochloric acid, at a temperature from 20° to 80° C.

A second method (method B) to obtain the compounds of formula (I') comprises an intramolecular cyclization reaction of derivatives of general formula (VII)

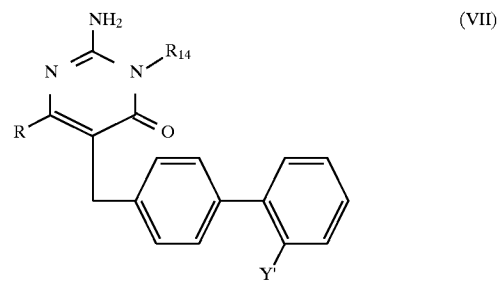

in which:
R has the same meanings as in formulae (I) and (I'), Y' has the same meanings as in formula (III), R$_{14}$ can be —(CH$_2$)$_n$—CR$_3$R$_4$X' or —CR$_3$R$_4$—(CH$_2$)$_n$Q, wherein Q and X' have the same meanings as in formula (IV), R$_3$, R$_4$ and n have the same meanings as in formula (I) and (I'), and, if necessary, subsequent transformation of the residue Y' into the residue Z' wherein Z' has the meanings as in formulae (I) and (I') as described for method A.

The reaction can be carried out as reported in method A or it can be effected in apolar solvents, such as benzene, toluene, CHCl$_3$ in the presence of catalytic amounts of an acid, preferably p-toluenesulfonic acid.

The compounds of general formula (VII) are prepared by alkylation of the compounds of formula (III), their amino group being suitably protected, with compounds of general formula (IV), in which preferably at least one of the meanings of Q and X' is halogen, and subsequently removing the protecting group of the resulting intermediates compounds of general formula (VIII)

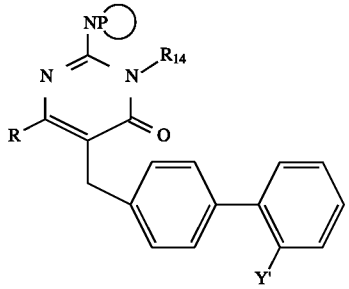
(VIII)

in which:

R, R$_{14}$, Y' have the same meanings as in formula (VII), P is a protecting group selected from acyl, phthalimido, arylmethylene, dialkylaminomethylene groups.

The alkylation reaction can be carried out in aprotic solvents such as DMF, D.MSO, NMP, THF or ethyl ether in the presence of bases such as alkali metal hydrides, alkoxides or carbonates, at temperatures from −20° C. to +30° C. If oxygen-alkylation products form, they can be separated by conventional chromatographic techniques.

The protection and the deprotection can be performed by per se known methods. For example, in the case of dialkylamino methylene derivatives, the protection can be effected reacting the compounds of formula (III) with a dialkylformamide acetal of general formula (VIII)

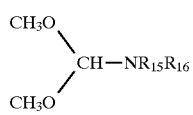
(VIII)

wherein:

R$_{15}$ and R$_{16}$ are straight or branched lower alkyl, in an aprotic solvent, preferably DMF, at temperatures from 20° C. to 80° C.

The protecting group can be removed by a strong acid, preferably HCl, at temperatures from 20° to 100° C.

A third method (method C) comprises reacting the compounds of formula (VI) with compounds of formula (IX) or the salts thereof

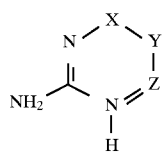
(IX)

in which:

X, Y, Z have the same meanings as in formulae (I) and (I'), to give compounds of formula (I) and (I') in which Z' is the same as Y' and subsequent transformation, if necessary, of the residue Y' into the residue Z', wherein Z' has the meanings as in formulae (I) and (I'), as described for method A.

The reaction is carried out in lower alcohols, such as methanol, ethanol, isopropanol, in the presence of acid catalysts, such as acetic or p-toluenesulfonic acids or in acetic or polyphosphoric acids, at temperatures from 60° C. to the boiling temperatures of the solvents.

A fourth method (method D) to obtain the compounds (I) and (I') in which Z' is a group of formula (IIa) or (IIb), comprises reacting the compounds of general formula (X) and (X')

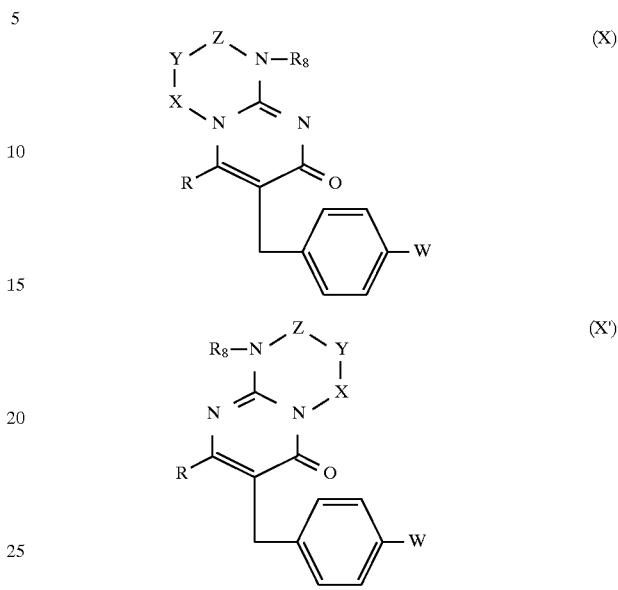
(X)

(X')

in which:

R, R$_8$, X, Y, Z have the same meanings as in formulae (I) and (I'), W can be bromine, iodine, methanesulfonyloxy, toluenesulfonyloxy or trifluoromethanesulfonyloxy, with compounds of general formula (XI)

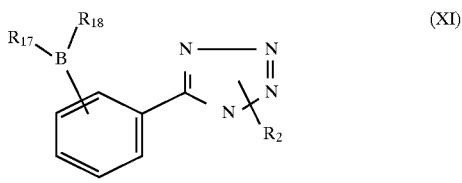
(XI)

in which:

R$_{17}$ and R$_{18}$ are independently chlorine, bromine, hydroxy or C$_1$–C$_4$ alkoxy, R$_2$ can be methyl or a protecting group, such as triphenylmethyl.

The reaction can be carried out in solvents, such as benzene, toluene, ethyl ether, THEF, dioxane, acetonitrile, ethanol, methanol, water or in the mixtures thereof at temperatures from 20° to 150° C., preferably from 60° to 90° C., in the presence of suitable transition metal derivatives, such as NiCl$_2$(PPh$_3$)$_2$, PdCl$_2$(PPh$_3$)$_2$, Pd(PPh$_3$)$_4$, tris(dibenzylideneacetone)dipalladium and of bases, such as Na$_2$CO$_3$, K$_2$CO$_3$, alkali or alkaline-earth metal hydroxides or alkoxides, tertiary amines such as triethylamine, optionally in the presence of phase transfer catalysts.

If the residue R$_2$ is triphenylmethyl, it can be removed as reported in method A.

The compounds of formula (X) and (X') are prepared analogously to the compounds of formula (I) and (I'), according to the methods A and B reported above, starting from B-ketoesters of formula (VI), in which T is the same as W.

The compounds of general formula (XI) are prepared according to the procedures described by V.Snieckus et al. in J.Org.Chem. 1991,56,3763–3768 and references therein cited, for example, by ortho metallation with lithium alkyls and subsecuent interchange with trialkoxy boronates, starting from 5-phenyl-2-triphenylmethyltetrazole.

The compounds described in the present invention act as antagonists at the A II receptor level. For the characterization and the evaluation of the effectiveness of the compounds of the invention, in vitro tests (such as the inhibition of the A II-induced contraction in the rabbit aorta and the displacement of $^{125}$I-Sar$^1$-Ile$^8$-AT II or [$^3$H] AT II in the rat adrenal cortex) and an in vivo test (the inhibition of the A II-induced pressory response in the ganglio-blocked normotensive rat) were selected. The compounds of invention have shown a remarkable activity in the above tests; for example, in the in vitro tests, a number of compounds turned out to have pA$_2$ or pK$_B$ values higher than 6.5, whereas they showed to have a Ki<1 $\mu$M in the receptor binding test.

For example the compound 5-butyl-3-methyl-6-[[2'-(1H-tetrazol-5-yl)biphenyl-4-yl]methyl]imidazo[1,2-a]pyrimidin-2,7-dione (ex.6) has shown Ki - 5 nM and PK$_B$ - 10.4.

The compounds (I) or the pharmaceutically acceptable salts thereof can be used in pharmaceutical preparations, alone or in a mixture with pharmaceutically acceptable excipients, for the oral or parenteral administrations. Suitable excipients are for example starch, lactose, glucose, arabic gum, stearic acid and the like. The pharmaceutical preparations can be in solid form such as tablets, capsules or suppositories or in liquid form, such as solutions, suspensions or emulsions.

Moreover, if administered parenterally, the pharmaceutical preparations can be in form of sterile solutions.

The compounds (I) can be administered in unit doses ranging from 1 to 100 to patients suffering from cardiac and vascular disorders, such as hypertension, acute and chronic cardiac decompensation, intraocular hypertension. However, a use can be envisaged also for other disorders, such as secondary hyperaldosteronism, pulmonary hypertension, renal diseases (glomerulonephritis, diabetic nephropathy) or vascular disorders (hemicrania, Raynaud's disease).

The following examples further illustrate the invention. M.p. are not corrected; the identity of the substances was established by means of elementary analysis (C, H, N) and IR, UV, NMR (200 MHz) and mass spectroscopies. Flash chromatographies (FC) were carried out on silica gel according to the procedures by W. C. Still, J.Org.Chem. 43, 2923 (1978).

EXAMPLE 1

Methyl 2-[(2'-methoxycarbonylbiphenyl-4-yl)methyl]-3-oxoheptanoate 2.3 g of methyl 3-oxoheptanoate dissolved in 10 ml of anhydrous THF are dropped into a suspension of 0.22 g of 80% NaH in 30 ml of anhydrous THF, under nitrogen atmosphere. When bubbling is over, the clear solution is slowly added with 2.22 g of 4-bromomethyl-2'-methoxycarbonylbiphenyl dissolved in 10 ml of anhydrous THF. After 15 minutes, the residue is taken up with water and adjusted to acid pH with acetic acid. The mixture is extracted with AcCEt, washed with a NaCl saturated solution, dried over Na$_2$SO$_4$ and the solvent is evaporated off under reduced pressure. The residue is purified by FC (eluent hexane-AcOEt 8:2), to obtain 2.6 g of a clear oil (93% yield).

$^1$H-NMR (CDCl$_3$) $\delta$: 0.86 (t,3H); 1.15–1.62 (m,4H) ; 2.25–2.65 (m,2H); 3.20 (d,2H); 3.63 (s,3H); 3.71 (s,3H); 3.84 (t,1H); 7.12–7.58 (m,7H); 7.78 (dd,1H).

Analogously are prepared:

methyl 2-[(2'-cyanobiphenyl-4-yl)methyl]-3-oxoheptanoate.

methyl 2-[[2'-[N-triphenylmethyl-(1H-tetrazol-5-yl)]biphenyl-4-yl]methyl]-3-oxoheptanoate.

methyl 2-[(2'-methoxycarbonylbiphenyl-4-yl)methyl]-3-oxohexanoate.

methyl 2-[(2'-tert-butoxycarbonylbiphenyl-4-yl)methyl]-3-oxoheptanoate.

methyl 2-[(4-bromophenyl)methyl]-3-oxoheptanoate.

methyl 2-[(4-iodophenyl)methyl]-3-oxoheptanoate.

EXAMPLE 2

2-Amino-6-butyl-5-[[2'-[N-triphenylmethyl-(1H-tetrazol-5-yl)]biphenyl-4-yl]methyl]pyrimidin-4-one A suspension of 0.45 g of guanidine hydrochloride and 0.25 g of CH$_3$ONa in 10 ml of tert-butanol is added, under magnetic stirring and nitrogen atmosphere, with a solution of 1.5 g of methyl 2-[[2'-[N-triphenylmethyl-(1H-tetrazol-5-yl) ]biphenyl-4-yl methyl]-3-oxoheptanoate in 20 ml of tert-butanol. After 5 h under reflux, the suspension is evaporated under reduced pressure and the residue is taken up in H$_2$O and extracted with AcOEt. The organic phase is washed with a NaCl saturated solution and dried over Na$_2$SO$_4$, to yield, upon evaporation under reduced pressure, 1.8 g of a yellow oil which is purified by FC (eluent CH$_2$Cl$_2$—MeOH 95:5) , to obtain 1.1 g of a spongy solid (73% yield).

$^1$H-NMR (DMSO-D$_6$) $\delta$: 0.77 (t,3H); 1.08–1.42 (m,4H); 2.22 (t,2H); 3.63 (s,2H); 6.35 (s,2H); 6.84–7.12 (m,9H); 7.22–7.65 (m,13H); 7.75 (dd,1H); 10.80 (s,1H).

Analogously are prepared:

2-amino-6-propyl-5-[[2'-[N-triphenylmethyl-(1H-tetrazol-5-yl) ]biphenyl-4-yl]methyl]pyrimidin-4-one.

2-amino-6-butyl-5-[(2'-cyanobiphenyl-4-yl)methyl]pyrimidin-4-one (m.p.=>250° C.).

2-amino-6-butyl-5-[(2'-methoxycarbonylbiphenyl-4-yl)methyl]pyrimidin-4-one (m.p.=252°–254° C.).

2-amino-6-butyl-5-[(2'-tert-butoxycarbonylbiphenyl-4-yl)methyl]pyrimidin-4-one.

2-amino-5-[(4-bromophenyl)methyl]-6-butylpyrimidin-4-one (m.p.=>250° C.).

2-amino-5-[(4-iodophenyl)methyl]-6-butylpyrimidin-4-one (m.p.=>250° C.).

EXAMPLE 3

6-Butyl-2-chloroacetylamino-5-[(2'-methoxycarbonylbiphenyl-4-yl)methyl]pyrimidin-4-one.

A solution of 0.4 g of 2-amino-6-butyl-5-[(2'-methoxycarbonylbiphenyl-4-yl)methyl]pyrimidin-4-one in, 10 ml of anhydrous DMF is added in succession with 0.1 g of chloroacetic acid, 0.21 g of DCC and 0.17 g of HOBT. After 8 h under magnetic stirring, the resulting solid is filtered off and the solvent is evaporated under reduced pressure. The residue is taken up with H$_2$O and extracted with AcOEt. The organic phase is dried over Na$_2$SO$_4$ and evaporated under reduced pressure to obtain 0.47 g of a yellowish spongy solid which can be reacted without further purification.

$^1$H-NMR (CDCl$_3$) $\delta$: 0.91 (t,3H); 1.22–1.62 (m,4H); 2.56 (t,2H); 3.63 (s,3H); 3.91 (s,2H); 4.25 (s,2H); 7.15–7.58 (m,7H); 7.79 (dd,1H).

Analogously are prepared:

2-(2-bromopropionylamino)-6-butyl-5-[(2'-methoxycarbonylbiphenyl-4-yl)methyl]pyrimidin-4-one.

2-(3-bromopropionylamino)-6-butyl-5-[[2'-[N-triphenylmethyl-(1H-tetrazol-5-yl)]biphenyl-4-yl]methyl]pyrimidin-4-one.

2-(2-bromopropionylamino)-6-butyl-5-[[2'-[N-triphenylmethyl-(1H-tetrazol-5-yl)]biphenyl-4-yl]methyl]pyrimidin-4-one.

[$^1$H-NMR (CDCl$_3$) δ: 0.88 (t,3H); 1.08–1.78 (m,4H); 1.86 (d,3H); 2.47 (t,2H); 3.79 (s,2H); 4.64 (q,1H); 6.85–7.05 (m,9H); 7.20–7.50 (m,13H); 7.78 (dd,1H)].

2-(2-bromobutyrylamino)-6-butyl-5-[[2'-[N-triphenylmethyl-(1H-tetrazol-5-yl)]biphenyl-4-yl]methyl]pyrimidin-4-one.

[$^1$H-NMR (CDCl$_3$) δ: 0.88 (t,3H); 1.07 (t,3H); 1.20–1.70 (m,4H); 1.98–2.32 (m,2H); 2.45 (t,2H); 3.78 (s,2H); 4.40 (t,1H); 6.86–7.08 (m,9H); 7.19–7.48 (m,13H); 7.88 (dd,1H)].

2-(4-bromobutyrylamino)-6-butyl-5-[[2'-[N-triphenylmethyl-(1H-tetrazol-5-yl)]biphenyl-4-yl]methyl]pyrimidin-4-one.

2-(2-bromo-2-methylpropionylamino)-6-butyl-5-[[2'-[N-triphenylmethyl-(1H-tetrazol-5-yl)]biphenyl-4-yl]methyl]pyrimidin-4-one.

2-(2-bromo-3-methylbutyrylamino)-6-butyl-5-[[2'-(N-triphenylmethyl-(1H-tetrazol-$^5$-yl))biphenyl-4-yl]methyl]pyrimidin-4-one.

($^1$H-NMR (CDCl$_3$) δ: 0.88 (t,3H); 1.08 (d,6H); 1.20–1.65 (m,4H); 2.25–2.52 (m,4H); 3.73 (s,2H) ; 4.34 (d,1H) 6.85–7.08 (m,9H) ; 7.18–7.48 (m,13H) ; 7.78 (dd,1H)].

2-(2-bromo-2-cyclopropylacetylamino)-6-butyl-5-[[2'-[N-triphenylmethyl-(1H-tetrazol-5-yl)]biphenyl-4-yl]methyl]pyrimidin-4-one.

2-(2-bromopropionylamino)-6-butyl-5-[[2'-cyanobiphenyl-4-yl)methyl]pyrimidin-4-one.

($^1$H-NMR (CDCl$_3$) δ: 0.90 (t,3H); 1.05–1.85 (m,4H); 1.86 (d,3H); 2.60 (t,2H); 3.94 (s,2H); 4.73 (q,1H); 7.22–7.72 (m,8H)].

2-bromoacetylamino-5-[(2'-methoxycarbonylbiphenyl-4-yl)methyl]-6-propylpyrimidin-4-one.

2-(2-bromopropionylamino)-6-propyl-5-[[2'-[N-triphenylmethyl-(1H-tetrazol-5-yl)]biphenyl-4-yl]methyl]pyrimidin-4-one.

2-[(3-bromo-2,2-dimethyl)propionylamino]-6-butyl-5-[[2'-[N-triphenylmethyl-(1H-tetrazol-5-yl)]biphenyl-4-yl]methyl]pyrimidin-4-one.

[$^1$H-NMR (CDCl$_3$) δ: 0.88 (t,3H); 1.40 (s,6H); 1.20–1.70 (m,4H); 2.42 (t,2H); 3.67 (s,2H); 3.78 (s,2H); 6.84–7.06 (m,9H); 7.15–7.48 (m,13H); 7.78 (dd,1H)]

2-(2-bromopropionylamino)-6-butyl-5-(4-iodophenyl)pyrimidin-4-one.

[$^1$H-NMR (CDCl$_3$) δ: 0.90 (t,3H); 1.10–1.80 (m, 4H); 1.87 (d,3H); 2.54 (t,2H); 3.81 (s,2H); 4.67 (q,1H); 6.99 (d,2H); 7.56 (d,2H)).

2-(2-bromopropionylamino)-5-(4-bromophenyl)-6-butyl pyrimidin-4-one ($^1$-NMR (CDCl$_3$) δ: 0.90 (t,3H); 1.20–1.80 (m,4H); 1.90 (d,3H), 2.50 (t,2H); 3.81 (s,2H); 4.53 (q,1H); 7.10 (d,2H); 7.37 (d,2H) ].

7-butyl-6-[[2'-[N-triphenylmethyl-(1H-tetrazol-5-yl)]biphenyl-4-yl]methyl]imidazo[1,2-a]pyrimidin-2,5-diione.

7-butyl-3-methyl-6-[[2'-[N-trihenylmethyl-(1H-tetrazol-5-yl)]biphenyl-4-yl methyl]imidazo[1,2-a]pyrimidin-2,5-dione.

7-butyl-3,3-dimethyl-6-[[2'-[N-triphenylmethyl-(1H-tetrazol-5-yl)]biphenyl-4-yl]methyl]imidazo[1,2-a]pyrimidin-2,5-dione.

7-butyl-3-ethyl-6-[[2'-[N-triphenylmethyl-(1H-tetrazol-5-yl)]biphenyl-4-yl]methyl]imidazo[1,2-a]pyrimidin-2,5-dione.

7-butyl-3-isopropyl-6-[[2'-[N-triphenylmethyl-(1H-tetrazol-5-yl)]biphenyl-4-yl]methyl]imidazo[1,2-a]pyrimidin-2,5-dione.

7-butyl-3-cyclopropyl-6-[[2'-[N-triphenylmethyl-(1H-tetrazol-5-yl)]biphenyl-4-yl]methyl]imidazo[1,2-a]pyrimidin-2,5-one.

8-butyl-3,4-dihydro-7-[[2'-[N-triphenylmethyl-(1H-tetrazol-5-yl)]biphenyl-4-yl]methyl]pyrimido[1,2-a]pyrimidin-2,6-dione.

EXAMPLE 4

5-butyl-6-[(2'-cyanobiphenyl-4-yl)methyl]-3-methylimidazo[1,2-a]pyrimidin-2,7-dione (regioisomer A)

7-butyl-6-[(2'-cyanobiphenyl-4-yl)methyl]-3-methylimidazo[1,2-a]pyrimidin-2,5-dione (regioisomer B)

A suspension of 0.14 g of 80% NaH in 20 ml of anhydrous THF is added, under nitrogen atmosphere with stirring, with a solution of 1 g of 2-(2-bromopropionylamino)-6-butyl-5-[(2'-cyanobiphenyl-4-yl)methyl]pyrimidin-4-one in 20 ml of anhydrous THF. When bubbling is over and after three hours under reflux, the solvent is evaporated unde- reduced pressure. The residue is taken up in H$_2$O and acidified to pH 1 with diluted HCl. The resulting white solid is filtered off and washed with water. The separation of the two regioisomers is carried out by FC (eluent CH$_2$Cl$_2$—CH$_3$OH 95:5). 0.19 g of a product with a higher Rf (regioisomer B) and 0.18 g of a product with a lower Rf (regioisomer A) are obtained, whose structures are assigned by NMR analysis (NOE experiments) (45% total yield).

A) $^1$H-NMR (CDCl$_3$) δ: 0.90 (t,3H); 1.22–1.70 (m,4H); 2.05 (s,3H); 2.69 (t,2H); 3.92 (s,2H); 7.30–7.80 (m,8H).

B) $^1$H-NMR (DMSO-D$_6$) δ: 0.85 (t,3H); 1.15–1.55 (m,4H); 1.50 (d,3H); 2.53 (t,2H); 3.79 (q,2H); 4.52 (q,1H); 7.25–7.72 (m,7H); 7.93 (d,1H).

Analogously are prepared:

5-butyl-6-[(2'-methoxycarbonylbiphenyl-4-yl)methyl]imidazo[1,2-a]pyrimidin-2,7-dione (m.p.—218°–222° C.).

5-butyl-3-methyl-6-[(2'-methoxycarbonylbiphenyl-4-yl)methyl]imidazo[1,2-a]pyrimidin-2,7-dione.

6-[(2'-methoxycarbonylbiphenyl-4-yl)methyl]-5-propylimidazo[1,2-a]pyrimidin-2,7-dione.

3-methyl-5-propyl-6-[[2'-[N-triphenylmethyl-(1H-tetrazol-5-yl)]biphenyl-4-yl]methyl]imidazo[1,2-a]pyrimidin-2,7-dione.

5-butyl-6-[[2'-[N-triphenylmethyl-(1H-tetrazol-5-yl)]biphenyl-4-yl]methyl]imidazo(1,2-a)pyrimidin-2,7-dione.

5-butyl-3-methyl-6-[[2'-[N-t-iphenylmethyl-(1H-tetrazol-5-yl)]biphenyl-4-yl]methyl]imidazo[1,2-a]pyrimidin-2,7-dione.

5-butyl-3-ethyl-6-[[(2'-[N-triphenylmethyl-(1H-tetrazol-5-yl)]biphenyl-4-yl]methyl]imidazo[1,2-a]pyrimidin-2,7-dione.

5-butyl-3-isopropyl-6-[[2'-[N-triphenylmethyl-(1H-tetrazol-5-yl)]biphenyl-4-yl]methyl)imidazo[1,2-a]pyrimidin-2,7-dione.

5-butyl-3-cyclopropyl-6-[[(2'-[N-triphenylmethyl-(1H-tetrazol-5-yl)]biphenyl-4-yl]methyl]imidazo[1,2-a]pyrimidin-2,7-dione.

5-butyl-3,3-dimethyl-6-[[2'-[N-triphenylmethyl-(1H-tetrazol-5-yl)]biphenyl-4-yl]methyl]imidazo[1,2-a]pyrimidin-2,7-dione.

6-butyl-3,4-dihydro-7-[[(2'-[N-triphenylmethyl-(1H-tetrazol-5-yl)]biphenyl-4-yl]methyl]pyrimido[1,2-a]pyrimidin-2,8-dione.

6-butyl-3,4-dihydro-3,3-dimethyl-7-[[2'-[N-triphenylmethyl-(1H-tetrazol-5-yl)]biphenyl-4-yl]methyl]pyrimido[1,2-a]pyrimidin-2,8-dione.

5-butyl-6-(4-iodophenyl)-3-methyl-imidazo[1,2-a]pyrimidin-2,7-dione.

6-(4-bromophenyl)-5-butyl-3-methyl-imidazo-[1,2-a]pyrimidin-2,7-dione.

7-butyl-6-[(2'-methoxycarbonylbiphenyl-4-yl)methyl]imidazo[1,2-a]pyrimidin-2,5-dione.

7-butyl-3-methyl-6-[(2'-metroxycarbonylbiphenyl-4-yl)methyl]imidazo[1,2-a]pyrinidin-2,5-dione.

6-[(2'-methoxycarbonylbiphenyl-4-yl)methyl]-7-propylimidazo[1,2-a]pyrimidin-2,5-dione.

3-methyl-7-propyl-6-[[2'-[N-triphenylmethyl-(1H-tetrazol-5-yl)]biphenyl-4-yl]methyl]imidazo[1,2-a]pyrimidin-2,5-dione.

7-butyl-6-[[2'-[N-triphenylmethyl-(1H-tetrazol-5-yl]biphenyl-4-yl]methyl]imidazo[1,2-a]pyrimidin-2,5-dione.

7-butyl-3-methyl-6-[[2'-[N-triphenylmethyl-(1H-tetrazol-5-yl)]biphenyl-4-yl]methyl]imidazo[1,2-a]pyrimidin-2,5-dione.

7-butyl-3-ethyl-6-[[2'-[N-triphenylmethyl-(1H-tetrazol-5-yl)]biphenyl-4-yl]methyl]imidazo[1,2-a]pyrimidin-2,5-dione.

7-butyl-3-isopropyl-6-[[2'-[N-triphenylmethyl-(1H-tetrazol-5-yl) ]biphenyl-4-yl)methyl]imidazo[1,2-a]pyrimidin-2,5-dione.

7-butyl-3-cyclopropyl-6-[[2'-[N-triphenylmethyl-(1H-tetrazol-5-yl)]biphenyl-4-yl]methyl]imidazo[1,2-a]pyrimidin-2,5-dione.

7-butyl-3,3-dimethyl-6-[[2'-(N-triphenylmethyl-(1H-tetrazol-5-yl)]biphenyl-4-yl]methyl]imidazo[1,2-a]pyrimidin-2,5-dione.

8-butyl-3,4-dihydro-7-([2'-[N-triphenylmethyl-(1H-tetrazol-5-yl)]biphenyl-4-yl]methyl]pyrimido[1,2-a]pyrimidin-2,6-dione.

8-butyl-3,4-dihydro-3,3-dimethyl-7-[[2'-[N-triphenylmethyl-(1H-tetrazol-5-yl)biphenyl-4-yl]methyl]pyrimido[1,2-a]pyrimidin-2,6-dione.

7-butyl-6-(4-iodophenyl)-3-methyl-imidazo[1,2-a]pyrimidin-2,5-dione.

6-(4-bromophenyl)-7-butyl-3-methyl-imidazo[1,2-a]pyrimidin-2,5-dione.

EXAMPLE 5

5-Butyl-6-((2'-carboxybiphenyl-4-yl)methyl]imidazo[1,2-a]pyrimidin-2,7-dione.

A solution of 0.17 g of 5-butyl-6-[(2'-methoxycarbonylbiphenyl-4-yl)methyl]imidazo[1,2-a]pyrimidin-2,7-dione in 2 ml of MeOH is added with 32 mg of NaOH dissolved in 0.05 ml of H$_2$O. After 24 h under reflux, the solvent is evaporated under reduced pressure and the residue is taken up in H$_2$O and acidified to pH 5, to separate a solid which is filtered off and washed thoroughly with H$_2$O. The purification is carried out by FC (eluent CH$_2$Cl$_2$—MeOH—AcOH 89:10:1), to obtain 85 mg of a white solid (51% yield; m.p.=220°–222° C.).

Analogously are prepared:

5-butyl-6-[(2'-carboxybiphenyl-4-yl)methyl]-3-methylimidazo[1,2-a]pyrimidin-2,7-dione (m.p.=209°–210° C.).

5-butyl-6-[(2'-carboxybiphenyl-4-yl)methyl]imidazo-[1,2-a]pyrimidin-3,7-dione (m.p.=120°–125° C. dec.)

5-butyl-6-[(2'-carboxybiphenyl-4-yl)methyl]-3-methylimidazo[1,2-a]pyrimidin-7-dione (m.p.=>250° C.).

7-butyl-6-[(2'-carboxybiphenyl-4-yl)methyl]imidazo-[(1,2-a]pyrimidin-2,5-dione.

7-butyl-6-[(2'-carboxybiphenyl-4-yl)methyl]-3-methylimidazo[1,2-a]pyrimidin-2,5-dione.

6-[(2'-carboxybiphenyl-4-yl)methyl]-7-propylimidazo[1,2-a]pyrimidin-2,5-dione.

6-[(2'carboxybiphenyl-4-yl)methyl]-5-propylimidazo[1,2-a]pyrimidin-2,7-dione.

2-amino-4-butyl-1-carboxymethyl-5-[[2'-[N-triphenylmethyl-(1H-tetrazol-5-yl)]biphenyl-4-yl]methyl]pyrimidin-6-one.

2-amino-4-butyl-1-(1-carboxyethyl)-5-[[2'-[N-triphenylmethyl-(1H-tetrazol-5-yl)]biphenyl-4-yl]methyl]pyrimidin-6-one.

EXAMPLE 6

5-Butyl-3-methyl-6-[[2'-(1H-tetrazol-5-yl)biphenyl-4-yl]methyl]imidazo[1,2-a]pyrimidin-2,7-dione A solution of 0.2 g of 5-butyl-3-methyl-6-[[2'-[N-triphenylmethyl-(1H-tetrazol-5-yl)]biphenyl-4-yl]methyl]imidazo[1,2-a]pyrimidin-2,7-dione in 6 ml of AcOH and 2 ml of H$_2$O is stirred at room temperature for 5 h, then is evaporated under reduced pressure. The residue is taken up into H$_2$O, adjusted to pH 8 with diluted NaOH and extracted with AcOet. The aqueous phase is acidified to pH 5 with AcOH, to separate a solid which is filtered off and washed with H$_2$O, to obtain 0.1 g of a white solid (80% yield, m.p=192°–194° C. dec.).

Analogously are prepared:

3-methyl-5-propyl-6-[[2'-(1H-tetrazol-5-yl)biphenyl-4-yl]methyl]imidazo[1,2-a]pyrimidin-2,7-dione.

5-butyl-6-([2'-(1H-tetrazol-5-yl)biphenyl-4-yl)methyl]imidazo[1,2-a]pyrimidin-2,7-dione (m.p=201°–205° C. dec.).

5-butyl-3-ethyl-6-[[2'-(1H-tetrazol-5-yl)biphenyl-4-yl]methyl]imidazo[1,2-a]pyrimidin-2,7-dione (m.p=206°–207° C. dec.).

5-butyl-3-isopropyl-6-[[2'-(1H-tetrazol-5-yl)biphenyl-4-yl]methyl]imidazo[1,2-a]pyrimidin-2,7-dione (m.p=214°–216° C. dec.).

5-butyl-3-cyclopropyl-6-[[2'-(1H-tetrazol-5-yl)biphenyl-4-yl]methyl]imidazo[1,2-a]pyrimidin-2,7-dione.

5-butyl-3,3-dimethyl-6-[[2'-(1H-tetrazol-5-yl)biphenyl-4-yl]methyl]imidazo[1,2-a]pyrimidin-2,7-dione.

6-butyl-3,4-dihydro-7-[[2'-(1H-tetrazol-5-yl)]biphenyl-4-yl]methyl]pyrimido[1,2-a]pyrimidin-2,8-dione.

6-butyl-3,4-dihydro-3,3-dimethyl-7-[[2'-(1H-tetrazol-5-yl)biphenyl-4-yl methyl]pyrimido[1,2-a]pyrimidin-2,8-dione.

7-butyl-3-methyl-6-[[2'-(1H-tetrazol-5-yl)biphenyl-4-yl]methyl]imidazo(1,2-a)pyrimidin-2,5-dione.

3-methyl-7-propyl-6-[[2'-(1H-tetrazol-5-yl)biphenyl-4-yl]methyl]imidazo(1,2-a]pyrimidin-2,5-dione.

7-butyl-6-[[2'-(1H-tetrazol-5-yl)biphenyl-4-yl]methyl]imidazo[1,2-a]pyrimidin-2,5-dione.

7-butyl-3-ethyl-6-[[2'-(1H-tetrazol-5-yl)biphenyl-4-yl]methyl]imidazo[1,2-a]pyrimidin-2,5-dione.

7-butyl-3-isopropyl-6-[[2'-(1H-tetrazol-5-yl)biphenyl-4-yl]methyl)imidazo[1,2-a]pyrimidin-2,5-dione.

7-butyl-3-cyclopropyl-6-[[2'-(1H-tetrazol-5-yl)biphenyl-4-yl]methyl]imidazo(1,2-a]pyrimidin-2,5-dione.

7-butyl-3,3-dimethyl-6-[[2'-(1H-tetrazol-5-yl)biphenyl-4-yl]methyl]imidazo[1,2-a]pyrimidin-2,5-dione.

8-butyl-3,4-dihydro-7-[[2'-(1H-tetrazol-5-yl)biphenyl-4-yl]methyl]pyrimido[1,2-a]pyrimidin-2,6-dione.

8-butyl-3,4-dihydro-3,3-dimethyl-7-[[2'-(1H-tetrazol-5-yl)biphenyl-4-yl]methyl]pyrimido[1,2-a]pyrimidin-2,6-dione.

5-butyl-6-[[2'-(1H-tetrazol-5-yl)biphenyl-4-yl]methyl]imidazo[1,2-a]pyrimidin-3,7-dione.

5-butyl-2-methyl-6-[[2'-(1H-tetrazol-5-yl)biphenyl-4-yl]methyl]imidazo[1,2-a]pyrimidin-3,7-dione.

5-butyl-3-methyl-6-[[2'-(1H-tetrazol-5-yl)biphenyl-4-yl]methyl)imidazo[1,2-a]pyrimidin-7-one.

7-butyl-2-methyl-6-[[2'-(1H-tetrazol-5-yl)biphenyl-4-yl]methyl]imidazo [1,2-a]pyrimidin-5-one.

7-butyl-6-[[2'-(1H-tetrazol-5-yl)biphenyl-4-yl]methyl]imidazo[1,2-a]pyrimidin-5-one.

EXAMPLE 7

7-Butyl-3-methyl-6-[[2'-(1H-tetrazol-5-yl)biphenyl-4-yl]methyl]imidazo[1,2-a]pyrimidin-2,5-dione A solution of 0.2 g of 7-butyl-6-((2'-cyanobiphenyl-4-yl)methyl]-3-methylimidazo[1,2-a]pyrimidin-2,5-dione in 4 ml of toluene and 1 ml of DMF is added with 38 mg of sodium azide and 0.17 ml of tributylstannyl chloride. After 72 h under reflux, the solvent is evaporated under reduced pressure and the residue is taken up in a NaOH diluted solution and extracted with toluene. The aqueous phase is acidified to pH 5 with AcOH, to separate a white solid which is filtered off and washed first with $H_2O$, and then with a mixture of hexane-toluene to obtain g 0.1 of a white solid, after crystallization (45% yield).

Analogously is prepared:

5-butyl-3-methyl-6-[[2'-(1H-tetrazol-5-yl)biphenyl-4-yl]methyl]imidazo[1,2-a]pyrimidin-2,7-dione.

EXAMPLE 8

5-Butyl-3-methyl-6-[[2'-methoxycarbonylbiphenyl-4-yl)methyl]imidazo[1,2-a]pyrimidin-7-one.

A solution of 0.3 g of 2-amino-6-butyl-5-[(2'-methoxycarbonylbiphenyl-4-yl) methyl]pyrimidin-4-one in 6 ml of DMF is added under stirring with 61 μl of chloroacetone. After 18 h under stirring at 100° C., the solvent is evaporated under reduced pressure. The residue is taken up into water to separate a solid which is filtered and purified by FC (eluent $CH_2Cl_2$—$CH_3OH$ 97:3), to obtain 90 mg of a spongy solid (27% yield).

$^1$H-NMR (CDCl$_3$) δ: 0.89 (t,3H); 1.22–1.62 (m,4H); 2.36 (d,3H); 2.68 (t,2H); 3.62 (s,3H); 4.04 (s,2H); 7.12–7.56 (m,8H); 7.78 (dd,1H).

Analogously are prepared:

5-butyl-6-[(2'-methoxycarbonylbiphenyl-4-yl)methyl]imidazo(1,2-a]pyrimidin-3,7-dione.

[$^1$H-NMR (CDCl$_3$) : 0.90 (t,3H); 1.22–1.75 (m,4H); 2.69 (t,2H); 3.64 (s,3H); 3.93 (s,2H); 4.51 (s,2H); 7.15–7.52 (m,7H); 7.78 (dd,1H)].

5-butyl-6-[[2'-[N-triphenylmethyl-(1H-tetrazol-5-yl)]biphenyl-4-yl)methyl]imidazo[1,2-a]pyrimidin-3,7-dione.

5-butyl-2-methyl-6-[[2'-[N-triphenylmethyl-(1H-tetrazol-5yl) ]biphenyl-4-yl]methyl]imidazo[1,2-a]pyrimidin-3,7-dione.

5-butyl-3-methyl-6-[[2'-[N-triphenylmethyl-(1H-tetrazol-5-yl)]biphenyl-4-yl]methyl]imidazo[1,2-a)pyrimidin-7-one

EXAMPLE 9

6-butyl-2-dimethylaminomethyleneamino-5-[(2'-methoxycarbonylbiphenyl-4-yl)methyl pyrimidin-4-one A solution of 0.5 g of 2-amino-6-butyl-5-((2'-methoxycarbonylbiphenyl- 4-yl)methyl)pyrimidin-4-one in 8 ml of anhydrous DMF is added, with stirring and under nitrogen atmosphere, with 0.17 ml of dimethylformamide dimethylacetal. After 3 h at room temperature, the solvent is evaporated under reduced pressure, to obtain 0.57 g of a yellow solid.

$^1$H-NMR (CDCl$_3$) δ: 0.88 (t,3H. 1.15–1.62 (m,4H); 2.50 (t,3H) ; 3.07 (s,3H); 3.15 (s, 3H); 3.61 (s,3H); 3.91 (s,2H) ; 7.08–7.52 (m,7H); 7.76 (dd,1H); 8.60 (s,1H); 9.14 (s,1H).

Analogously are prepared:

2-dimethylaminomethylenamino-5-[(2'-methoxycarbonylbiphenyl-4-yl)methyl]-6-propylpyrimidin-4-one.

6-butyl-2-dimethylaminomethylenamino-5-[[2'-[N-triphenylmethyl-(1H-tetrazol-5-yl)]biphenyl-4-yl]methyl]pyrimidin-4-one.

[$^1$H-NMR (CDCl$_3$) δ: 0.86 (t,3H); 1.12–1.64 (m,4H); 2.42 (t,2R); 3.06 (s,3H); 3.14 (s,3H); 3.77 (s,2H); 6.85–7.10 (m,8H); 7.15–7.50 (m,14H); 7.83 (dd,1H); 8.57 (s,1H)].

2-dimethylaminomethylenamino-5-[[2'-[N-triphenylmethyl-(1H-tetrazol-5-yl)]biphenyl-4-yl]methyl]6-propylpyrimidin-4-one.

EXAMPLE 10

4-butyl-2-dimethylaminomethylenamino-5-[(2'-methoxycarbonylbiphenyl-4-yl)methyl]-1-methoxycarbonylmethylpyrimidin-6-one.

A suspension of 7 mg of 80% NaH in 1 ml of anhydrous THF is added with a solution of 0.1 g of 6-butyl-2-dimethylaminomethylenamino-5-[(2'-methoxycarbonylbiphenyl-4-yl)methyl]pyrimidin-4-one under nitrogen atmosphere and with magnetic stirring. When bubbling is over, the yellow clear solution is added with 21 μl of methyl bromoacetate and, after 30', the solvent is evaporated off under reduced pressure. The residue is purified by FC (eluent $CH_2Cl_2$—$CH_3OH$ 99:1), to obtain 92 mg of a yellow oil (84% yield).

¹H-NMR (CDCl₃) δ: 0.89 (t,3H); 1.22–1.66 (m,4H); 2.51 (t,2H); 3.04 (s,3H); 3.16 (s,3H); 3.61 (s,3H); 3.72 (s,3H); 3.94 (s,2H); 5.00 (s,2H); 7.10–7.52 (m,7H) 7.76 (dd,1H); 8.55 (s,1H).

Analogously are prepared:

2-dimethylaminomethylenamino-5-[(2'-methoxycarbonylbiphenyl-4-yl)methyl]1-methoxycarbonylmethyl-4-propylpyrimidin-6-one.

4-butyl-2-dimethylaminomethylenamino-5-((2'-methoxycarbonylbiphenyl-4-yl)methyl)-1-(1-methoxycarbonylethyl)pyrimidin-6-one.

4-butyl-2-dimethylaminomethylenamino-1-methoxycarbonylmethyl-5-[[2'-[N-triphenylmethyl-(1H-tetrazol-5-yl)]biphenyl-4-yl]methyl]pyrimidin-6-one.

(¹H-NMR (CDCl₃) δ: 0.87 (t,3H); 1.20–1.62 (m,4H); 2.43 (t,2H); 3.04 (s,3H); 3.16 (s,3H); 3.71 (s,3H); 3.80 (s,2H); 4.98 (s,2H); 6.85–7.10 (m,8H); 7.20–7.50 (m,14H); 7.77 (dd,1H); 8.54 (s,1H).

4-butyl-2-dimethylaminomethylenamino-1-(1-methoxycarbonylethyl)-5-((21-(N-triphenylmethyl-(lH-tetrazol-5-yl) ]biphenyl-4-yl]methyl]pyrimidin-6-one.

4-butyl-2-dimethylaminomethylenamino-1-(2-oxopropyl)-5-[[2'-[N-triphenylmethyl-(1H-tetrazol-5-yl))biphenyl-4-yl]methyl]pyrimidin-6-one.

4-butyl-2-dimethylaminomethylenamino-1-(2-methoxycarbonylethyl)- 5- [[2'-(N-triphenylmethyl-(1H-tetrazol-5-yl)]biphenyl-4-yl]methyl]pyrimidin-6-one.

4-butyl-2-dimethylaminomethylenamino-1-(2,2-dimethoxyethyl)-5-[[2'-[N-triphenylmethyl-(1H-tetrazol-5-yl)]biphenyl-4-yl]methyl]pyrimidin-6-one.

4-butyl-2-dimethylaminomethylenamino-1-(2-methyl-1-methoxycarbonylpropyl)-5-[[2'-[N-triphenylmethyl-(1H-tetrazol-4-yl)]biphenyl-4-yl)]methyl]pyrimidin-6-one.

4-butyl-2-dimethylaminomethylenamino-1-(1-methoxycarbonylpropyl)-5-[[2'-[N-triphenylmethyl-(1H-tetrazol-5-yl)]biphenyl-4-yl]methyl]pyrimidin-6-one.

4-butyl-1-(1-cyclopropyl-1-methoxycarbonylmethyl)-2-dimethylaminomethylenamino-5-[[2'-[N-triphenylmethyl-(1H-tetrazol-5-yl)]biphenyl-4-yl]methyl]pyrimidin-6-one.

4-butyl-2-dimethylaminomethylenamino-1-(3-methoxycarbonylpropyl)-5-[[2'-[N-triphenylmethyl-(1H-tetrazol-5-yl)]biphenyl-4-yl]methyl]pyrimidin-6-one.

4-butyl-2-dimethylaminomethylenamino-1-(1-methyl-1-methoxycarbonylethyl)-5-[[2'-[N-triphenylmethyl-(1H-tetrazol-5-yl)]biphenyl-4-yl]methyl]pyrimidin-6-one.

2-dimethylaminomethylenamino-1-(1-methoxycarbonylethyl)-5-[[2'-[N-triphenylmethyl-(1H-tetrazol-5-yl)]biphenyl-4-yl]methyl]-4-propylpyrimidin-6-one.

EXAMPLE 11

5-butyl-3-methyl-6-[[2'-[N-triphenylmethyl-(1H-tetrazol 5-yl)biphenyl-4-yl]methyl]imidazo[1,2-a]pyrimidin-2,7-dione Under nitrogen atmosphere, a suspension of 50 mg of 6-(4-bromophenyl)-5-butyl-3-methyl-imidazo[1,2-a] pyrimidin-2,7-dione, 70 mg of 2-[N-triphenylmethyl-(1 H-tetrazol-5-yl)]phenylboronic acid and 40 mg of K₂CO₃ in 6 ml of anhydrous toluene, vigorously stirred, is added with 14 mg of Pd (PPh₃)₄. After heating at 90° C. for 4 hours, 20 mg of catalyst was further added and heating is continued for 36 hours. The solution, diluted with AcOEt, is washed with aqueous solution of NaHCO₃, citric acid and NaCl, dried on Na₂SO₄ and evaporated to dryness. The residue is purified by FC (elmuent: CH₂Cl₂/CH₃OH 95:5) obtaining 20 mg of a white solid (yield 23%). The NMR data of the compound obtained in this example and in example 4 are identical,

[¹H-NMR (CDCl₃) δ: 0.91 (t,3H); 1.20–1.65 (m,4H); 1.59 (d,3H); 2.40 (t,2H); 3.76 (q,2H); 4.28 (q,1H); 6.85–7.12 (m,9H); 7.18–7.52 (m,13H); 7.86 (dd,1H).

We claim:

1. A compound of the general formulae (I) or (I') including tautomers and enantiomers

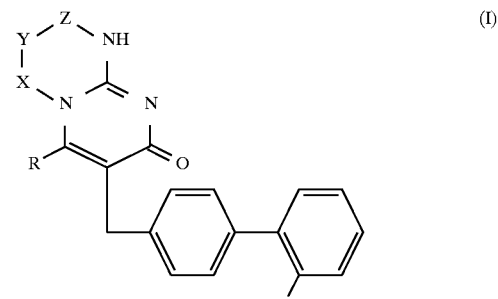

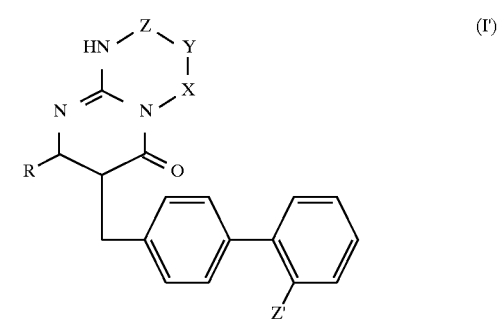

in which:

Z' is a tetrazole group of the general formulae (IIa) or (IIb)

R is a straight C₁–C₄ alkyl or cyclopropyl;

X, Y, Z form, together with the pyrimidone ring to which they are linked, a heterocyclic moiety selected from the group consisting of

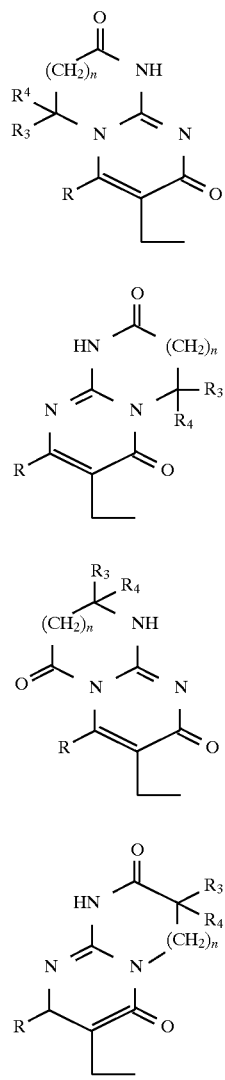

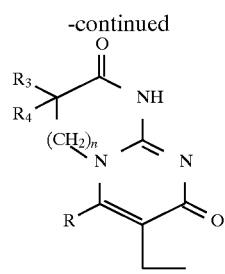

in which
n is 0 or 1
$R_3$ and $R_4$ are independently hydrogen or methyl; and the pharmaceutically acceptable acid and base salts thereof.

2. Compounds according to claim 1 selected from:
(a) 5-butyl-3-methyl-6-[[2'-(1H-tetrazol-5-yl)biphenyl-4-yl]methyl]imidazo[1,2-a]pyrimidin-2,7-dione
(b) 5-butyl-6-[[2'-(1H-tetrazol-5-yl)biphenyl-4-yl]methyl]imidazo[1,2-a]pyrimidin-2,7-dione
(c) 5-butyl-3-cyclopropyl-6-[[2'-(1H-tetrazol-5-yl)biphenyl-4-yl]methyl]imidazo[1,2-a]pyrimidin-2,7-dione
(d) 5-butyl-3,3-dimethyl-6-[[2'-(1H-tetrazol-5-yl)biphenyl-4-yl]methyl]imidazo[1,2a]pyrimidin-2,7-dione
(e) 7-butyl-3-methyl-6-[[2'-(1H-tetrazol-5-yl)biphenyl-4-yl]methyl]imidazo[1,2-a]pyrimidin-2,5-dione
(f) 7-butyl-6-[[2'-(1H-tetrazol-5-yl)biphenyl-4-yl]methyl]imidazo[1,2a]pyrimidin-2,5-dione
(g) 7-butyl-3-cyclopropyl-6-[[2'-(1H-tetrazol-5-yl)biphenyl-4-yl]methyl]imidazo[1,2-a]pyrimidin-2,5-dione
(h) 7-butyl-3,3-dimethyl-6-[[2'-(1H-tetrzol-5-yl)biphenyl-4-yl]methyl]imidazo[1,2a-]pyrimidin-2,5-dione.

3. A pharmaceutical composition endowed with A II antagonistic activity which comprises as the principal active ingredient an effective amount of a compound according to claim 1 together with a pharmaceutically acceptable carrier.

4. A process for the treatment of Angiotensine II-modulated diseases which comprises administering to a patient an effective dosage of a composition according to claim 3.

* * * * *